US012766014B2

United States Patent
(12) United States Patent
Cherubini et al.

(10) Patent No.: US 12,766,014 B2
(45) Date of Patent: Oct. 20, 2026

(54) PROSTHETIC DEVICE

(71) Applicants: FONDAZIONE ISTITUTO ITALIANO DI TECNOLOGIA, Genoa (IT); I.N.A.I.L. ISTITUTO NAZIONALE PER L'ASSICURAZIONE CONTRO GLI INFORTUNI SUL LAVORO, Rome (IT)

(72) Inventors: Andrea Cherubini, Genoa (IT); Michele Canepa, Genoa (IT); Nicolò Boccardo, Genoa (IT); Simone Traverso, Genoa (IT); Matteo Laffranchi, Genoa (IT); Lorenzo De Michieli, Genoa (IT); Emanuele Gruppioni, Rome (IT); Samuele De Giuseppe, Genoa (IT); Josephus Johannes Maria Driessen, Genoa (IT); Paolo Rossi, Genoa (IT)

(73) Assignees: FONDAZIONE ISTITUTO ITALIANO DI TECNOLOGIA, Genoa (IT); I.N.A.I.L. ISTITUTO NAZIONALE PER L'ASSICURAZIONE CONTRO GLI INFORTUNI SUL LAVORO, Rome (IT)

( * ) Notice: Subject to any disclaimer, the term of this patent is extended or adjusted under 35 U.S.C. 154(b) by 387 days.

(21) Appl. No.: 18/575,606

(22) PCT Filed: Jul. 1, 2022

(86) PCT No.: PCT/IB2022/056153
§ 371 (c)(1),
(2) Date: Dec. 29, 2023

(87) PCT Pub. No.: WO2023/275846
PCT Pub. Date: Jan. 5, 2023

(65) Prior Publication Data

US 2024/0293239 A1 Sep. 5, 2024

(30) Foreign Application Priority Data

Jul. 2, 2021 (IT) ........................ 102021000017537

(51) Int. Cl.
*A61F 2/70* (2006.01)
*A61F 2/50* (2006.01)
(Continued)

(52) U.S. Cl.
CPC .................. *A61F 2/70* (2013.01); *A61F 2/64* (2013.01); *A61F 2/741* (2021.08); *A61F 2/748* (2021.08);
(Continued)

(58) Field of Classification Search
CPC ........................................................ A61F 2/70
See application file for complete search history.

(56) References Cited

U.S. PATENT DOCUMENTS 11,617,665 B2 4/2023 Shin et al.
2006/0249315 A1* 11/2006 Herr ...................... A61F 2/6607 623/47
(Continued)

FOREIGN PATENT DOCUMENTS

AU 2011237357 A1 * 11/2012 ............... A61F 2/70
DE 102018126324 A1 * 4/2020 ............... A61F 5/01
(Continued)

OTHER PUBLICATIONS

International Search Report from corresponding PCT Application No. PCT/IB2022/056153, Oct. 25, 2022.
(Continued)

*Primary Examiner* — Jacqueline Woznicki
(74) *Attorney, Agent, or Firm* — Workman Nydegger

(57) ABSTRACT

A prosthetic device includes an articular actuator assembly including a reduction gearbox that includes an actuating part connected to an output of the reduction gearbox and an actuated part integral with a distal portion of the prosthetic device. The actuating part and the actuated part are provided with abutment and reciprocal fitting. The abutment surfaces are provided on at least one protrusion of the actuating part and on at least one protrusion of the actuated part. In a decoupled condition the protrusion of the actuating part is positioned angularly, spaced from the protrusion of the actuated part and constitutes an end stop for the extension of the distal portion and allows free flexion of the distal
(Continued)

portion. In a coupled condition the protrusions are in abutment with each other and actuate the relative rotation of the distal portion with respect to a proximal portion of the prosthetic device in extension.

8 Claims, 11 Drawing Sheets

(51) Int. Cl.
*A61F 2/64* (2006.01)
*A61F 2/68* (2006.01)
*A61F 2/74* (2006.01)

(52) U.S. Cl.
CPC ................. *A61F 2002/5004* (2013.01); *A61F 2002/5006* (2013.01); *A61F 2002/6836* (2013.01); *A61F 2002/701* (2013.01)

(56) References Cited

U.S. PATENT DOCUMENTS

| | | | | |
|---|---|---|---|---|
| 2007/0050044 A1 | | 3/2007 | Haynes et al. | |
| 2009/0299480 A1 | | 12/2009 | Gilbert et al. | |
| 2015/0182354 A1 | * | 7/2015 | Bonnet | A61F 2/70 623/26 |
| 2016/0158029 A1 | | 6/2016 | Kuiken et al. | |
| 2018/0194000 A1 | * | 7/2018 | Smith | B25J 9/0006 |
| 2024/0293239 A1 | * | 9/2024 | Cherubini | A61F 2/748 |

FOREIGN PATENT DOCUMENTS

| | | | | | |
|---|---|---|---|---|---|
| DE | 102018131698 A1 | * | 6/2020 | | A61F 2/68 |
| WO | WO-2006052954 A2 | * | 5/2006 | | F16D 57/002 |
| WO | WO-2006112774 A1 | * | 10/2006 | | A61F 2/6607 |
| WO | WO-2009015473 A1 | * | 2/2009 | | A61F 2/64 |
| WO | WO-2009067240 A1 | * | 5/2009 | | A61F 2/60 |
| WO | 2021002536 A1 | | 1/2021 | | |

OTHER PUBLICATIONS

Italian Search Report from corresponding IT Application No. 102021000017537, Mar. 11, 2022.

* cited by examiner

PROSTHETIC DEVICE

The present invention relates to a prosthetic device, capable of replacing at least part of a user's limb.

The prosthetic device comprises a proximal prosthetic portion adapted to be coupled to a user's limb segment and a distal prosthetic portion, the proximal prosthetic portion and the distal prosthetic portion being inter-connected by an articular portion.

The articular portion comprises an articular actuator assembly for rotatably driving in extension and/or flexion said distal portion with respect to said proximal portion around an axis of rotation.

A damper assembly is also provided, connected to said articular portion and adapted to absorb energy when a torque is applied between said proximal portion and said distal portion.

The articular actuator assembly is provided with a removable mechanical engagement element such that the actuator assembly can be switched from a coupled condition in which it rotatably drives said distal portion with respect to said proximal portion to a decoupled condition in which said distal portion is uniquely coupled to said damper for a predetermined rotation angle.

The device of the present invention is particularly suitable as a knee joint replacement and the following disclosure will focus on this type of application. Nevertheless, it is clear to the person skilled in the art that the invention can also be applied in other types of prosthetic devices relating to other joints.

The ultimate goal of lower limb prostheses is to reproduce the functions of the missing limb as faithfully as possible, implementing a plausible biomechanical behaviour based on the user's intention. To meet the functional needs, passive and semi-active prostheses, which do not have the capacity to provide active power to the joint, require a greater expenditure of energy on the part of the amputee compared to prostheses that have the possibility to provide active power. In most cases, these commercial prostheses involve the presence of a hydraulic, rotational (for example, Ottobock 3R80) or linear (for example, Ottobock C-LEG) damper.

The main priorities for the use of lower limb prostheses on the part of the amputee are related to comfort and reduced weights, reliability, low cost, and propulsion assistance in the most demanding activities (standing up, stairs, ramps etc.). Dissatisfaction with even some of these requirements often leads patients to abandon the prosthesis, or to use it in an unsatisfactory manner.

To try to solve these problems, knee prostheses have been designed as disclosed at the beginning, known to the state of the art. These prostheses have a passive dissipation element, so as to assist in the walking phase, and an active motorized element, parallel to the first, for activities that require its use (such as standing up, stairs, ramps etc.). For these activities, however, the prostheses currently on the market offer few solutions and are poorly appreciated due to weights, high costs and short battery life as a result of high consumption.

Document US 2009/0299480 A discloses a prosthetic device having a joint portion and a damping transmission assembly in operative communication with the joint portion. The damping transmission assembly includes a damping element that absorbs energy during flexion of the joint and releases it during joint extension. The articular portion further comprises an actuator assembly and a torque sensor.

The device disclosed, however, has high weight, reduced battery autonomy, low efficiency due to the direct coupling between brake and actuator, and noise at all times of operation because the motor cannot be disconnected. The device is also not satisfactorily anthropomorphic, has no mechanisms for the hardware safety of the device, and has a distance between the standard pyramidal coupling element and the high joint axis, which therefore does not allow for good alignment for all patients with respect to the natural axis.

Document US 2007/0050044 A1 describes a prosthetic leg with a regenerative prosthetic knee, i.e. one that is electronically controlled and can store energy from movement. The prosthetic knee can be passive, so it is only used to generate electricity, or active, whereby it can be used to assist gait as well as generate electricity. The prosthetic knee includes an electronic control system to regulate the overall function of the prosthetic leg, to distribute the electricity generated and to transfer excess electricity to one or more storage devices for later use.

The device disclosed, however, suffers from the lack of a mechanism that decouples the actuator/generator and the hydraulic cylinder, and this results in a very difficult passive walk, since the kinematic chain is always in gear, where the main problem is the reduction gearbox with high reduction ratios. This chain prevents the user from directly imparting movement to the prosthesis, and in fact causes the opposite behaviour. Undergoing an imposed movement does not make it easier for the patient, who has the unpleasant feeling of losing control of the device. The device is also very noisy at every stage, even during passive walking, due to the fact that the reduction gearbox is constantly engaging, and needs a dedicated system to transform and store the energy produced by passive walking.

WO 2021/002536 A1 D1 discloses a hybrid knee prosthesis comprising a hydraulic damper and an active drive module. When the prosthesis performs a rotation, the passive power from the damper and the active power from the actuating module can be provided selectively or simultaneously to the knee joint element by a clutch. The motor's rotational drive is provided by two pulleys, one coupling pulley and one return pulley, around which pulleys a drive cable is wound. The drive cable is actuated by a motor for a predetermined linear extension by means of a guide element, which can be connected and disconnected to the cable by means of a clutch module, preferably with a clamp that can be locked onto the cable and released from it. This complex mechanism significantly increases the size and weight of the prosthesis, which goes against the optimization requirements for easy use by the patient. The simple presence of the clutch also allows the active drive module to be connected and disconnected, but does not allow for fine-tuning of the respectively free and constrained movements of the joint according to the patient's walking or stair-climbing needs or rising from a sitting position.

The present invention aims to reduce the size and weight of the prosthesis, while increasing its autonomy.

The present invention aims to overcome the aforementioned disadvantages of the prostheses currently known with a prosthetic device as disclosed at the beginning, in which also the articular actuator assembly comprises an electric motor and a reduction gearbox, which reduction gearbox is connected at the input with the motor and at the output with said engagement element. The engagement element comprises an actuating part connected to the output of the reduction gearbox and an actuated part integral with the distal portion. The actuating part and the actuated part are respectively provided with abutment and reciprocal fitting surfaces arranged in radial planes with respect to said axis of rotation, which abutment surfaces are respectively provided on at least one protrusion of the actuating part and on at least one protrusion of the actuated part. Said protrusions have angular extensions such that in said decoupled condition the protrusion of the actuating part is positioned angularly spaced from the protrusion of the actuated part so as to constitute an end stop for the extension of the distal portion and allow the free flexion of the distal portion for a predetermined angular amplitude, while in said coupled condition the protrusions of the actuating part and the actuated part are respectively abutting each other so as to actuate the relative rotation of the distal portion with respect to the proximal portion in extension.

The organ that performs active assistance functions is therefore able to disengage automatically depending on the patient's activity, as a passive mechanical engagement is provided, allowing the joint to move freely within the angular range of physiological movement.

This allows a system capable of having the actuator assembly perform low speed and high active torque movements, while all other movements characterized by high speed and low torque, or low speed and high passive (i.e. braking) torque can be performed by the damper assembly alone.

The possibility of disengaging the actuator assembly makes it possible to identify a reduction gearbox with anthropometric dimensions such that it can be used on all tasks of the prosthesis and guarantee the correct autonomy.

Disengaging the actuator assembly from the damper assembly also makes it possible to reduce the weight and size of the prosthesis to the essentials, while at the same time guaranteeing the possibility of performing both tasks characterized by active energy contribution and tasks in which the energy exchanged is passive, thus optimising the efficiency of the device. The motor could be used for walking, but the mechanism leads to lower overall consumption and less stress on the drive shaft. Lower consumption also enables the use of smaller capacity batteries and thus reduced encumbrance.

The actuator assembly is then engaged on patient command only for the performance of active tasks (requiring active power but lower operating speeds), while for passive tasks (requiring power dissipation) it can be disengaged, while remaining physically present, and only the damper assembly is used.

The main advantages deriving from the invention are largely dependent on the use of a mechanical engagement element that enables decoupling between the actuator assembly and the damper assembly, as they are responsible for actuating the prosthesis in different operating phases. Therefore, fixed coupling between the two assemblies would lead to mutually antagonistic behaviour, should they be coupled, adding operational problems that would be difficult to manage except with advanced control techniques, leading to increased battery consumption.

In particular, in the absence of the engagement element, the actuator assembly should also follow the high-speed movements of the prosthesis, being permanently constrained to the joint. Among these movements there is the walking phase, in which the leg, no longer resting with the ground, swings in the rear direction. In this phase, during which the patient is able to impart movement to the prosthesis by swinging the hip, the leg needs high speed and low torque. In contrast, in activities that require active power to extend the leg (e.g. getting up from a chair or climbing stairs), the prosthesis needs high torques and low speeds. These two opposing requirements make it impossible to find a single reduction gearbox solution that fits within the required weight and size parameters.

Furthermore, in the absence of such an engagement element, the reduction gearbox would have to be in operation at all times, which would lead to very low efficiency and the necessary autonomy for the prosthesis would not be achieved, and/or the maximum weight/size of the battery would be exceeded. The perpetually engaged reduction gearbox would also produce noise that would be constant and socially unacceptable and hence a disincentive to use the prosthesis.

Since the activities in which the active part is required consist of a small percentage of the patient's daily activities, perpetual use of the active part would lead to its premature consumption, which in turn would lead to deterioration in the reliability of the system, without a functional reason.

Finally, having the two kinematic branches constantly engaged at the same time would greatly complicate the control of the prosthesis, which would have to manage two microcontrolled parts at the same time.

In one embodiment, one or more sensors and a control unit are provided, which control unit is connected with said sensors and is configured to set the actuator assembly in coupled or decoupled condition based on the data received from the sensors.

The control unit then performs a data-fusion based on what it receives from the sensors and automatically adjusts the engagement of the actuator unit accordingly. In this way, the prosthesis responds to external stresses imparted by the user's movements and provides active power only when necessary, leaving the actuator assembly disconnected in all other cases and only the damper assembly engaging.

In one embodiment, the control unit is configured to drive the motor in such a way that the actuating part is moved in real time to an angular position such that either the said coupled condition or the said decoupled condition is set.

In a further embodiment, the control unit is configured to actuate the motor such that when the patient is in a seated position the actuating part is in the said decoupled condition in a trailing mode such that said actuating part is maintained in real time at a substantially constant angular distance from the actuated part. During the patient's rise from said seated position the actuating part is brought into contact with the actuated part to set the said coupled condition, and when the patient has reached an upright position, the actuating part is brought into an angular getaway distance from the actuated part such as not to hinder walking.

If the patient returns to a sitting position, the damper assembly provides the necessary support until the joint angle corresponding to the patient's sitting position is reached, at which point the system returns to trailing mode.

According to an exemplary embodiment, both the actuating part and the actuated part each include protrusions that are symmetrical with respect to the axis of rotation, which protrusions of each part have at least two abutment surfaces angularly spaced 180° apart.

In one embodiment, said reduction gearbox assembly is a strain wave reduction gearbox.

In another embodiment, the output of the reduction gearbox constitutes the said actuating part and is provided with two said protrusions protracting in the direction of the actuated part, the actuated part being integral with the distal portion and provided with two circular sector slots in which the protrusions of the actuating part are inserted, said slots being separated from each other by an abutment element that constitutes two said protrusions of the actuated part.

According to a further exemplary embodiment, the damper assembly comprises a hydraulic cylinder provided with one or more valves actuated by said control unit. In this way, controlled damping is achieved.

The present invention, therefore, manages to obtain anthropometric dimensions, improved battery autonomy, and a guarantee of a wide range of performable activities supported by the prosthesis.

Compared to the known state-of-the-art prostheses, the power/energy density is significantly increased, and the simplicity of the engagement/disengagement mechanism enables ease of production, low cost and reduced maintenance, the latter also being ensured by the reduced use of active components present.

These and other features and advantages of the present invention will become clearer from the following disclosure of several embodiments illustrated, by way of example only, in the attached drawings, wherein.

Figure 8A:
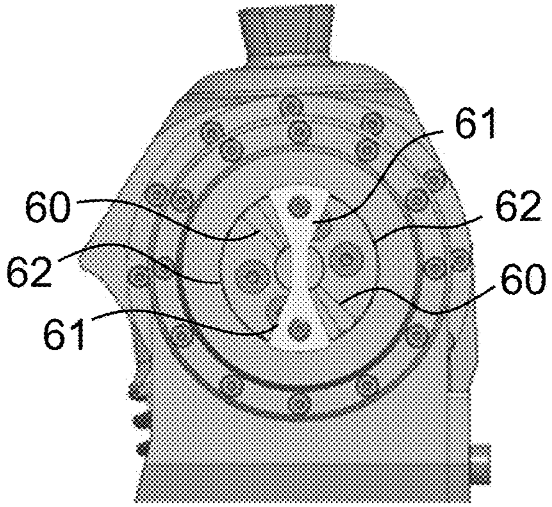
Figure 8B:
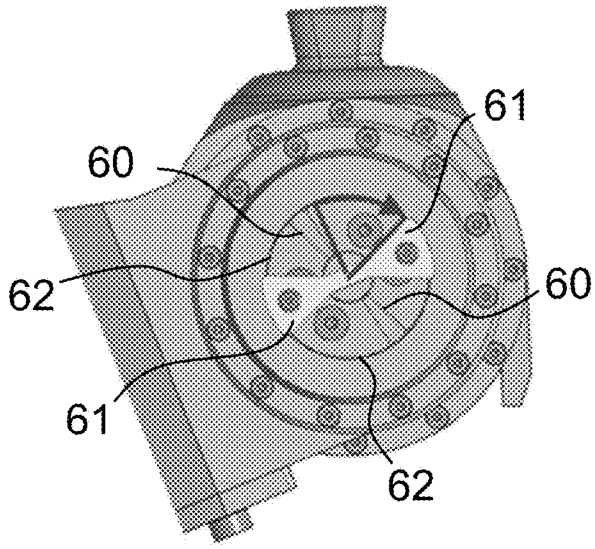
Figure 8C:
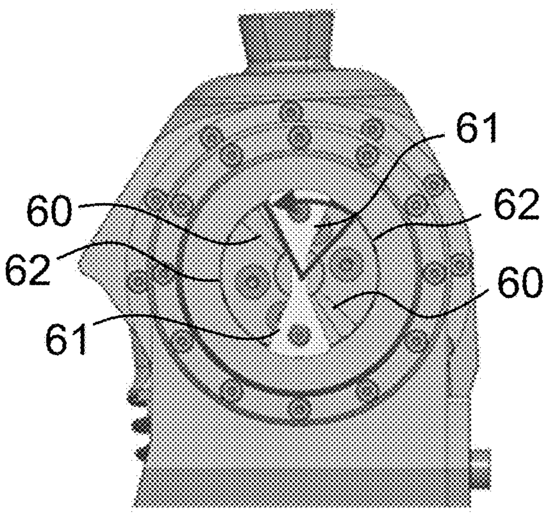
Figure 9:
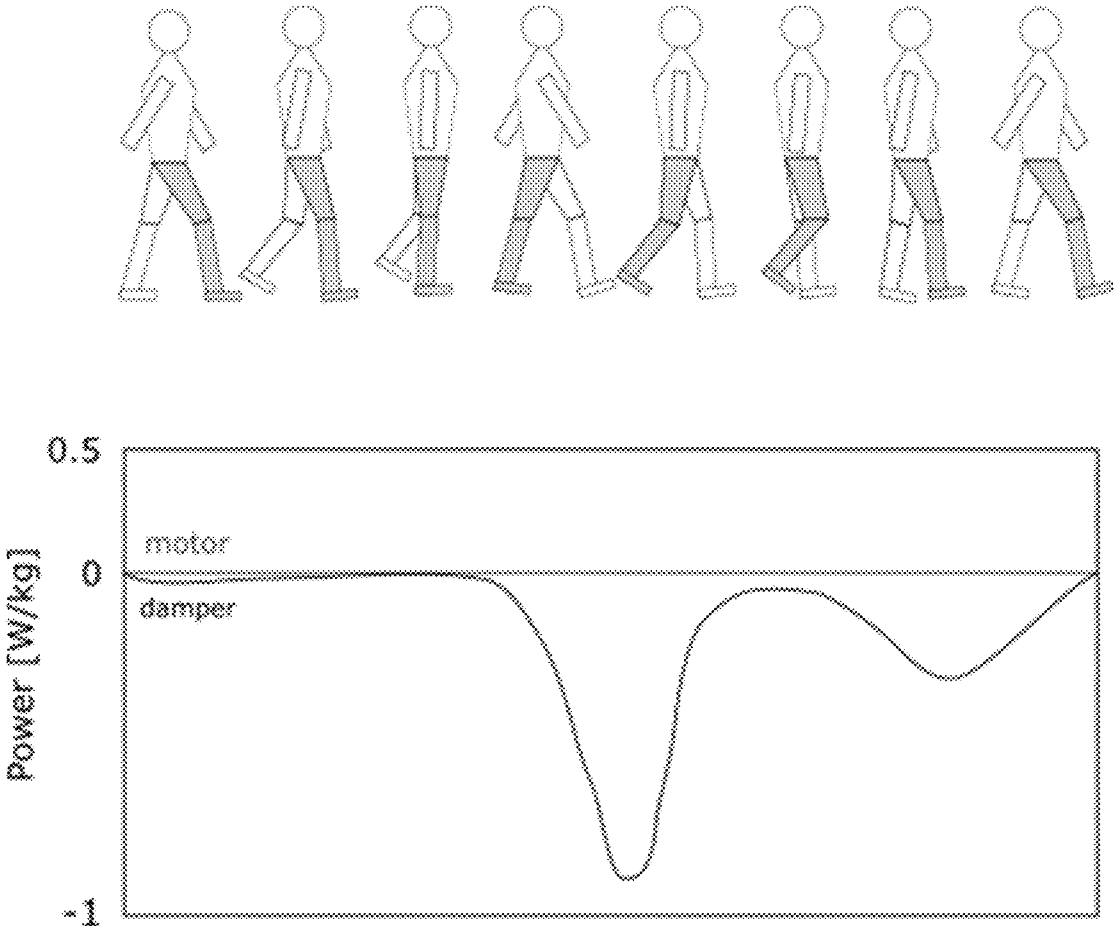
Figure 10A:
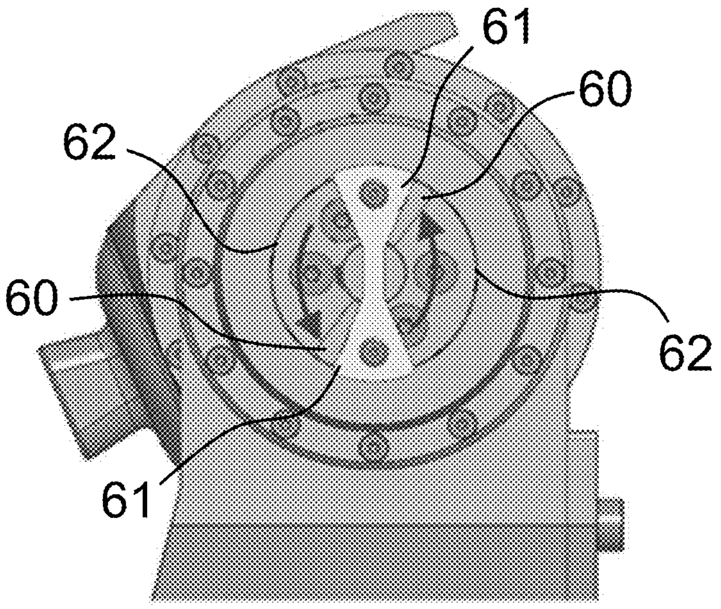
Figure 10B:
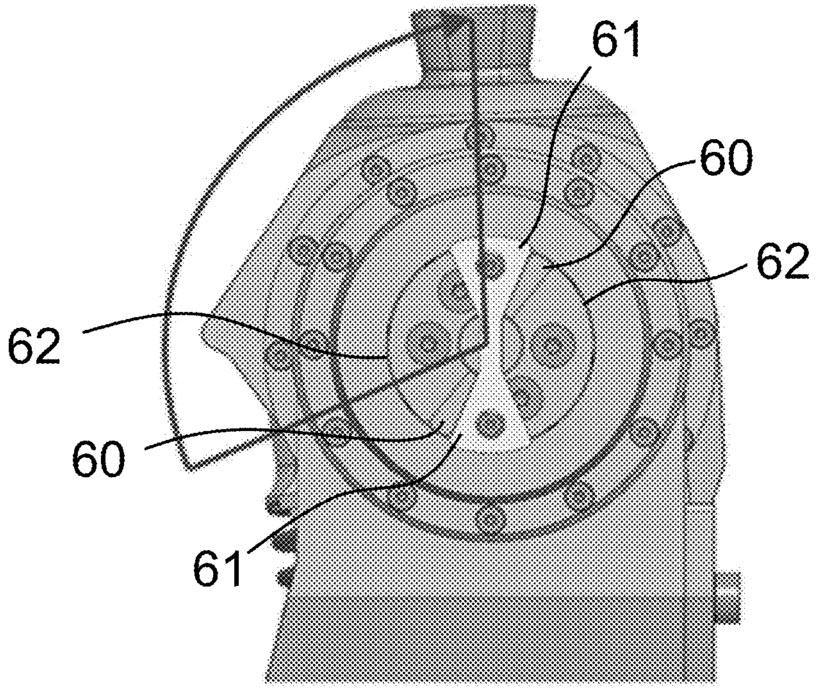
Figure 11:
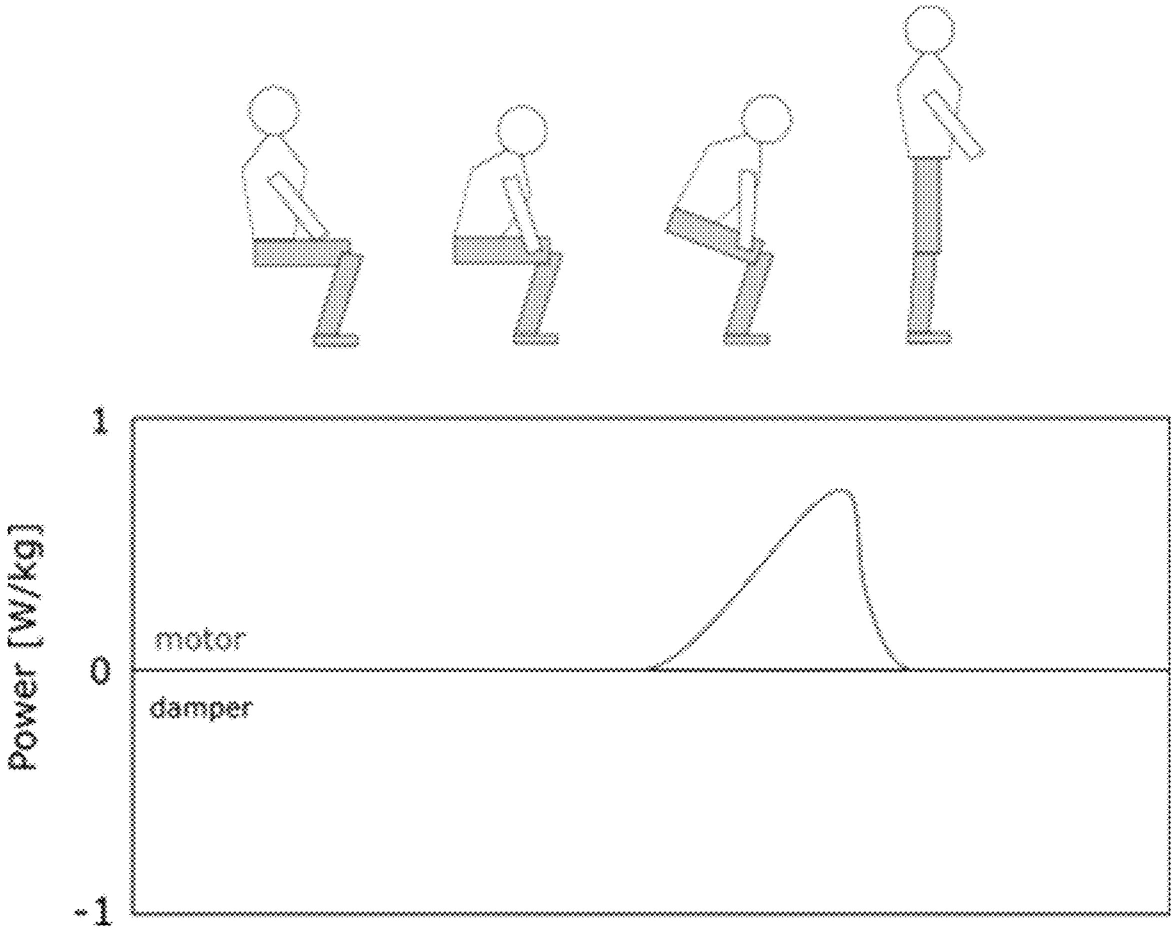
Figure 12:
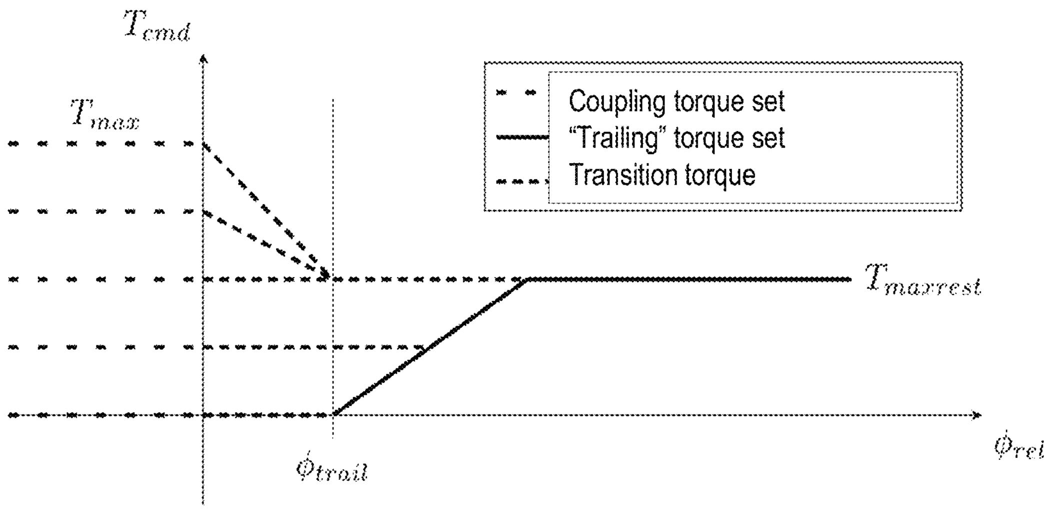

FIGS. 8*a*, 8*b* and 8*c* illustrate different stages of movement in the decoupled condition of the engagement element;

FIG. 9 illustrates the behaviour of the device during natural walking;

FIGS. 10*a* and 10*b* illustrate different stages of movement in the coupled condition of the engagement element;

FIG. 11 illustrates the behaviour of the device when the patient is rising from a seated position;

FIG. 12 illustrates the behaviour of the motor as a function of the angle of the joint.

The Figures illustrate a preferred exemplary embodiment of a knee prosthesis device according to the present invention, adapted to replace at least in part the lower limb of a user.

Figure 1:
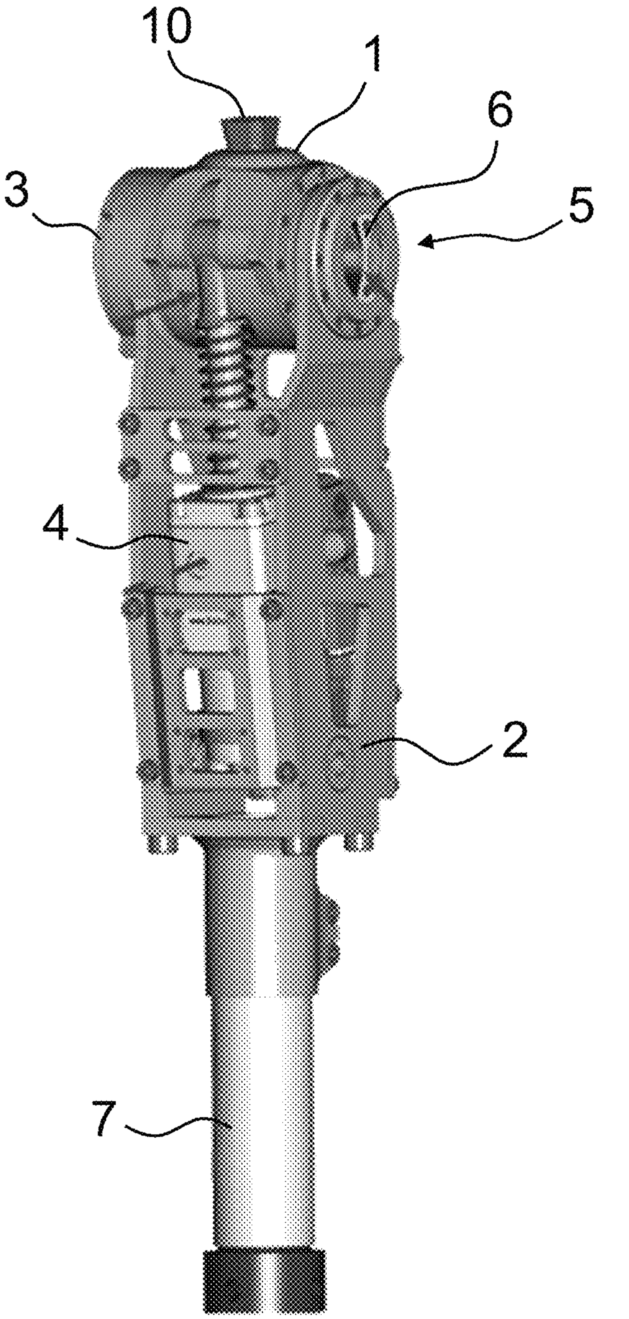
FIG. 1 illustrates an assembled view of the prosthetic device.

This "hybrid" type prosthesis, illustrated in the assembled condition in FIG. 1, is based on two parallel kinematic chains, the first capable of exchanging active energy, the second capable of passively dissipating energy and force-regulated electronically.

The device comprises a proximal prosthetic portion 1 capable of being coupled to a limb segment of the user by means of a pyramidal coupling element 10 and a distal prosthetic portion 2.

The proximal prosthetic portion 1 and the distal prosthetic portion 2 are inter-connected by means of a joint portion 3 or joint.

Figure 2:
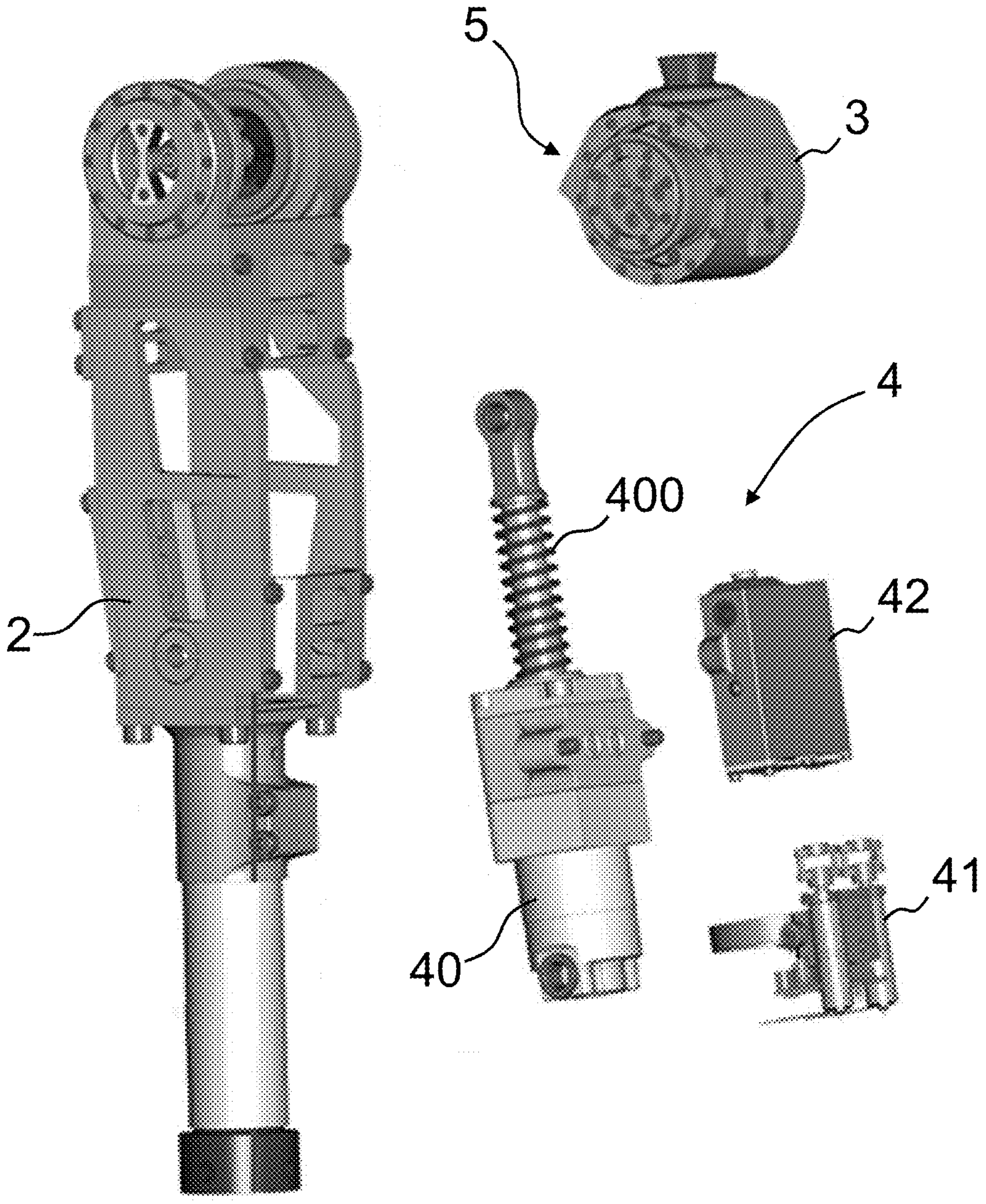
FIG. 2 illustrates an exploded view.

FIG. 2 shows an exploded view of the major components of the prosthetic device.

The articular portion 3 comprises an articular actuator assembly 5 for rotatably actuating in extension the distal portion 2 with respect to the proximal portion 1 around a rotation axis 30. The actuator assembly 5 constitutes said first kinematic chain, capable of exchanging active energy, and specifically comprises a joint actuated with an electric motor 50 coupled to a speed reduction gearbox 51.

Said second kinematic chain, capable of passively dissipating energy, is constituted by a damper assembly 4 connected to the articular portion 3 and adapted to absorb energy when a torque is applied between the proximal portion 1 and the distal portion 2. The damper assembly 4 is specifically constituted by a hydraulic unit, electronically regulated by means of motorized valves controlled in position.

The damper assembly 4 is composed of hydraulic cylinder 40, valve actuation motor assembly 41 and manifold 42.

The hydraulic cylinder 40 is a through-rod, double-chamber cylinder on which a 400 spring, external to the rod, is mounted to help the prosthesis return to a fully upright position following the walking swing.

The valve actuation motor unit 41 consists of two DC brush motors 410, which positionally adjust the opening of the valves in the circuit. There can be either one or two valves, in this case with the addition of a one-way passive valve, in the event that one-way operation of the circuit is desired, e.g. during the task of getting up from the chair. Monodirectionality is achieved by closing the active valve of the part of the circuit without the passive valve just mentioned, which constitutes the single branch active valve. With this configuration, when the patient stands up from the chair, for example, involuntary flexion of the prosthesis will be prevented, but only extension will be allowed, actuated by the reduction gearbox, as described in more detail below.

It is possible to use specific trajectories of the valve closure system, instead of opening and closing steps, so as to favour a much smoother and almost non-existent impact with the mechanical end stop. This brings a benefit in terms of noise, but also in terms of inertial reaction forces, which are less impulsive on the socket, i.e. on the part worn by the patient, and thus on the stump itself, thereby increasing embodiment and at the same time making the patient's walk even more natural.

The articular actuator assembly 5 is provided with a removable mechanical engagement element 6 such that the actuator assembly 5 is switchable from a coupled condition, in which it rotatably actuates the distal portion 2 with respect to the proximal portion 1, to a decoupled condition in which the distal portion 2 is uniquely coupled to the damper assembly 4 for a predetermined angle of rotation.

Figure 3:
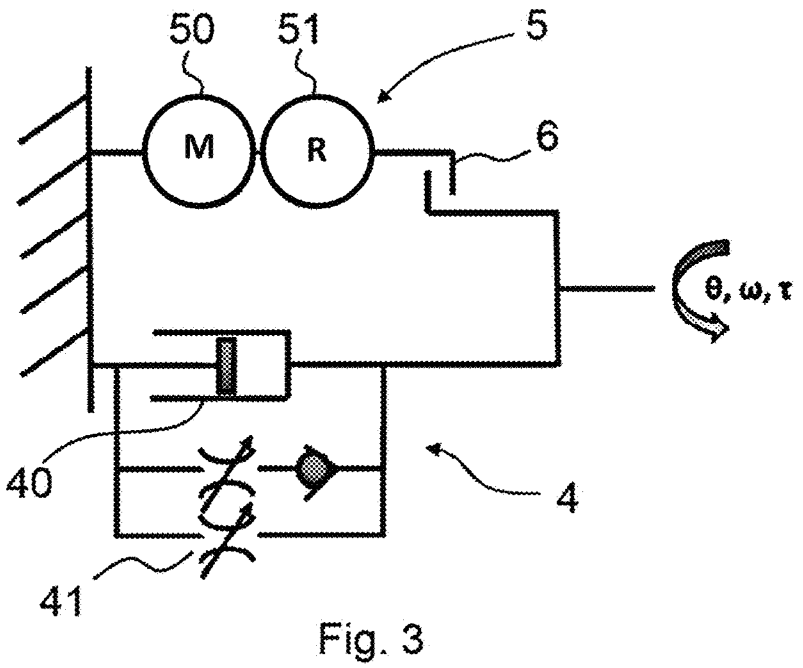
FIG. 3 illustrates a kinematic diagram of the device's operation.

FIG. 3 illustrates a diagram of the two kinematic chains of the prosthetic device placed parallel to each other. The actuator assembly 5 comprises a motor 50, preferably an electric motor, connected to a reduction gearbox 51, preferably a strain wave reduction gearbox. The actuator assembly 5 can be coupled or decoupled by means of the removable engagement element 6. The damper assembly 4 comprises said hydraulic cylinder 40 and said valve assembly 41.

The prosthesis must be capable of being used autonomously by the patient, which is why it is equipped with one or more sensors connected with a control unit comprising special control and power electronic boards, coupled with a rechargeable battery system with a BMS (Battery Management System) electronic board.

Figure 4:
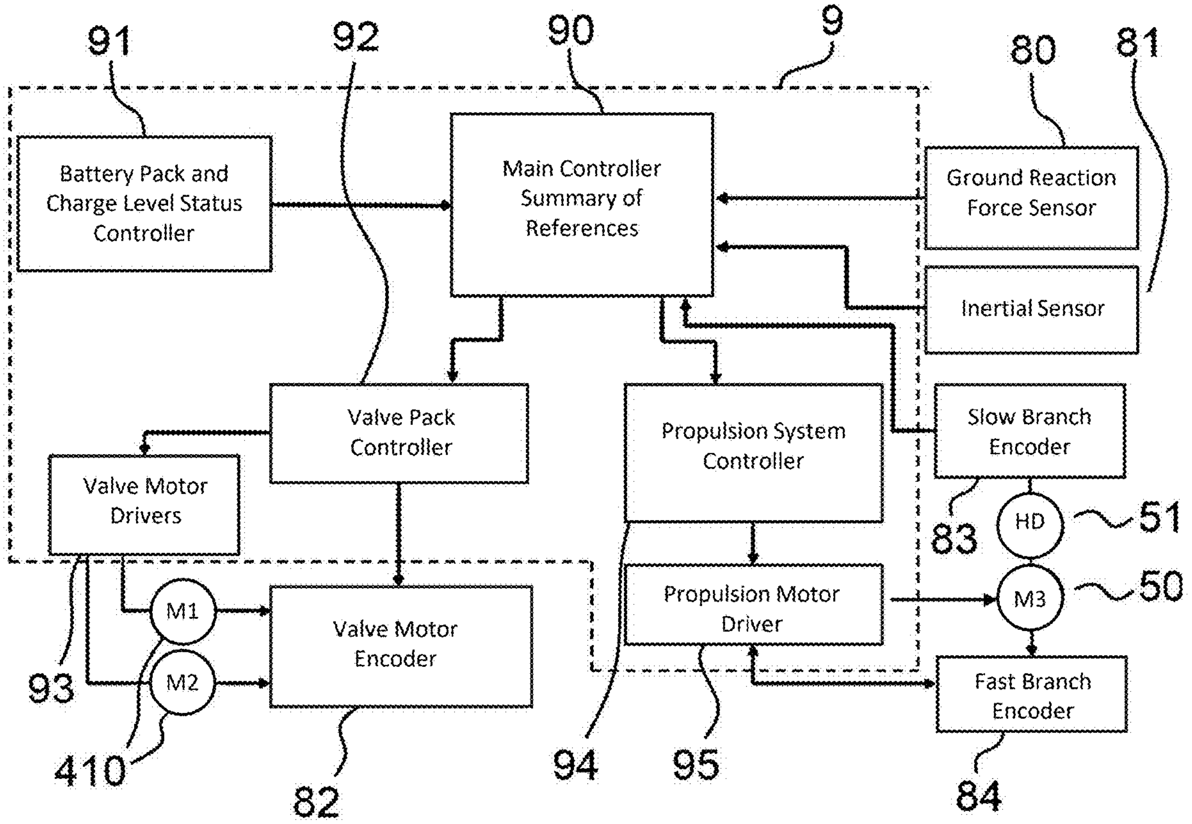
FIG. 4 illustrates a block diagram of the device's electronic architecture.

From an electronic point of view, the prosthetic device has a modular distributed architecture, illustrated in FIG. 4, formed by the said control unit 9 comprising a main controller summary of references 90, which may include a microprocessor, dedicated to synthesising the appropriate control signals towards the electric actuators, by means of a propulsion system controller 94 and a propulsion motor driver 95, and towards the hydraulic actuators, by means of a valve pack controller 92 and a valve motor driver 93, from the afferent sensor signals and from input received from a battery pack and charge level status controller 91.

The related sensors measure the physiological angle, the angular attitude in space, the coupling torque and the ground reaction force. Only part of these measurements can be predicted, as can additional sensors.

By physiological angle is meant the angle present between the proximal portion 1 and the distal portion 2. To detect the physiological angle, an encoder is used on the slow branch, i.e. on the reduction gearbox 51, which communicates with the microprocessor of the main controller summary of references 90.

By angular attitude in space is meant the angular position of the distal portion 2 with respect to gravity and, consequently, in combination with the detection of the above-mentioned physiological angle, also of the proximal portion 1. For the detection of the angular attitude in space, an inertial measurement unit (IMU) 81 integral with the distal portion 2 is provided.

Figure 5:
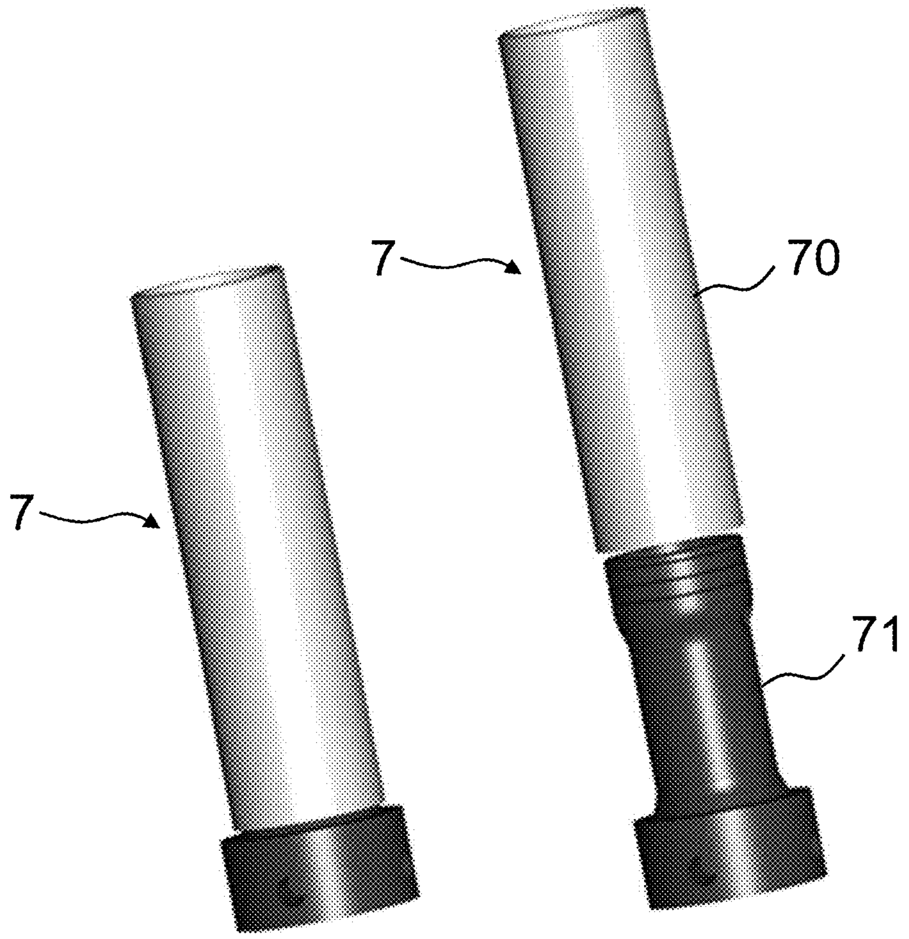
FIG. 5 shows an assembled and an exploded view of the distal end of the prosthetic device.
Figure 6:
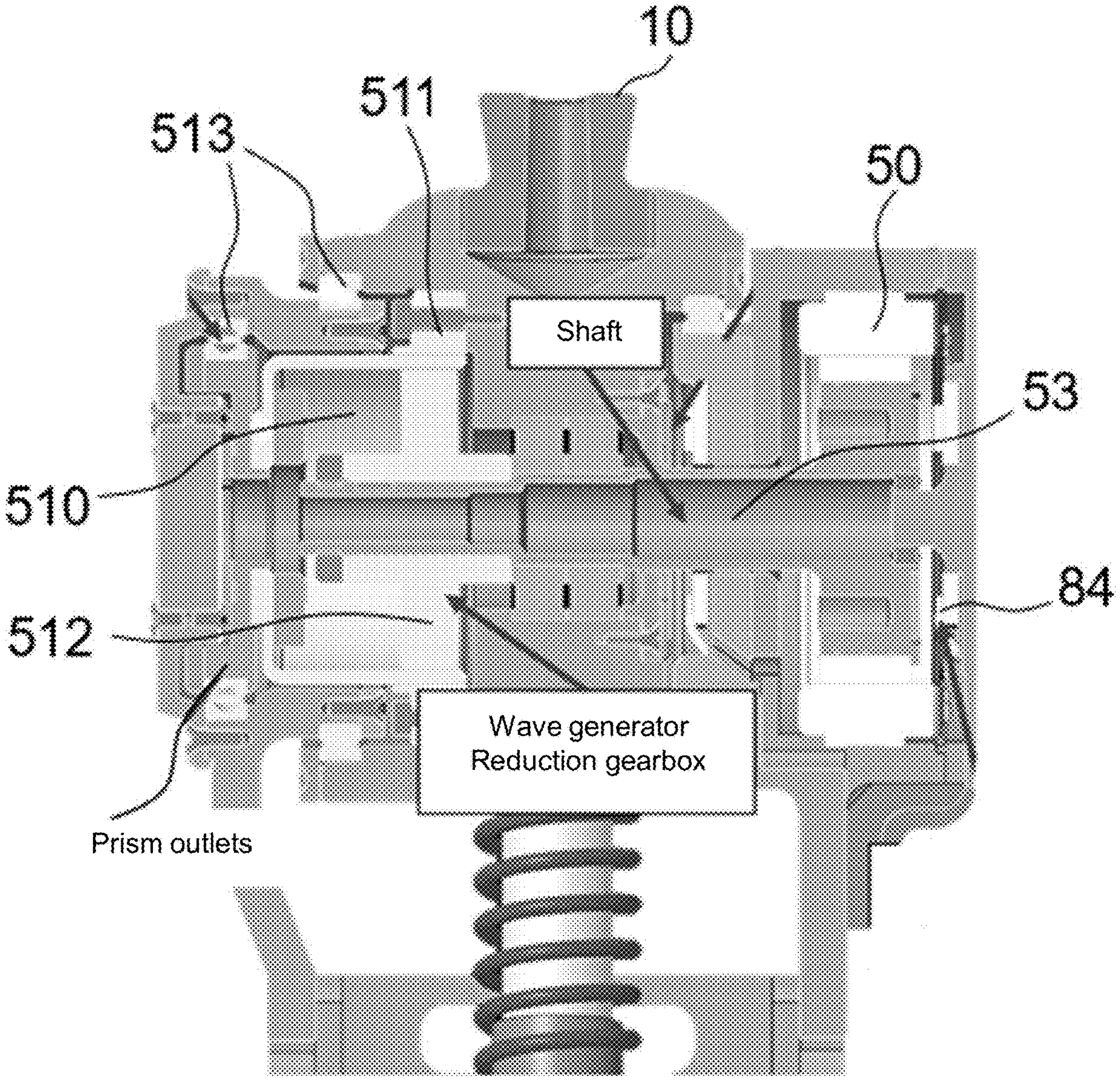
FIG. 6 shows a sectional view of the actuator assembly.
Figure 7:
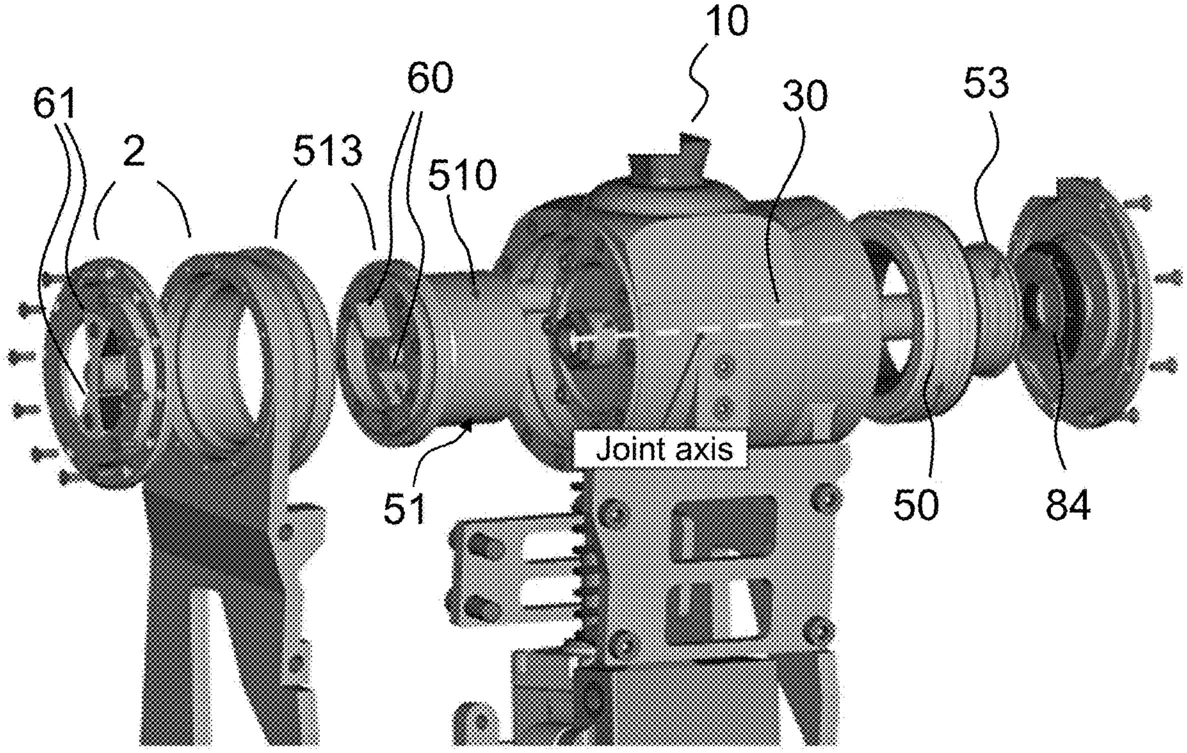
FIG. 7 illustrates an exploded view of the actuator assembly.

Finally, the essential component for detecting the forces applied by the patient in the gait, and thus the detection of stride, is the distal terminal 7, consisting of a connection tube 70 and a strain gauge sensor tube 71, at the bottom of the prosthesis. This strain gauge sensor tube 71, shown in FIG. 5, has a ground reaction force sensor 80, consisting of a double bridge of internal strain gauges, to detect forces and torques applied by the patient on the prosthesis.

There is also a power system based on lithium batteries, with its diagnostic and protection system.

With regard to control solutions, however, the device has been designed in order to be able to distinguish autonomously the tasks that the patient is performing and, consequently, identify the stage of the passage in which the prosthesis is located. The aim is therefore to make the prosthesis work together with the patient, thus minimizing the likelihood of running into undefined situations and, at the same time, identifying the situations that do or do not require motorization.

For this purpose, the control unit 9 performs a data-fusion based on what is received by the sensors and is configured to set the actuator assembly 5 in a coupled or decoupled condition based on said data-fusion.

In particular, the device, within the electronic architecture described above, combines the force and torque information from the reaction force sensor with the ground of the sensing tube 71 with the physiological position information of the coupling, i.e. obtained from the encoder 83 of the slow branch of the propulsion system and the encoder 84 of the fast branch i.e. of the motor 50, specifically the position upstream of the reduction stage 51 and the engagement element 6. It is then possible to identify the phase of the stride and the relative intention of the patient, also exploiting the inertial sensor 81 and simple mathematical computations, in order to make the device work collaboratively with the user.

The modularity of the electronic system makes it possible to add additional sensors aimed at improving the control of the prosthesis, such as electromyographic sensors integrated into the casing.

The valves 41 of the damper assembly 4 are actuated by the control unit 9 on the basis of signals detected by the sensors. The valve pack controller 92 receives valve condition data from an encoder 82 of the valve motors 410 and acts on the opening and closing of the valves by operating the valve motors 410 by means of a driver 93.

Due to the sensors, the system is therefore able to identify which task the patient is performing. This allows the control unit 9 to decide whether or not the use of the motor 50 is appropriate and, if necessary, to be able to operate it in the most physiological manner possible, the ultimate aim being to be able to apply the desired thrust without sudden impacts occurring or the system is hindering the patient's mobility.

In order to do this, the algorithm is based on a coupling of the position of the joint 3 with the position of the motor 50, so that in the session the latter is always ready to apply the desired thrust when requested, remaining vigilant as a result of a behaviour called "trailing". This behaviour ensures that the motor 50 is always active and follows the angle of the joint 3 in real time at a substantially constant angular distance, hence without interfering with the movement of the joint 3. At the moment the system identifies the patient's intention to stand up, the motor applies a force proportional to that detected by the sensor tube 71 and/or the speed of the movement made and/or the distance from the patient's standing angle.

Once the patient's rising movement is complete, the motor 50 moves to a getaway position so that it is not hindering walking activity, thus remaining inactive. Once the intention to sit has been identified, the hydraulic damping system constituted by the damper assembly 4 provides the support necessary for the descent and, once the joint 3 reaches the physiological seating angle, the motor is reactivated in its aforementioned "trailing" mode ready for the next upward movement.

As shown in FIG. 12, the entire process is based on configurable values such as the "trailing" angle, i.e. the angular distance that the motor 50 must maintain from the mechanical engagement element 6 to be at all times vigilant, and from the maximum torque to be applied. These values can be calibrated according to the patient in order to give a thrust that is as balanced as possible according to the needs of the healthy limb of the user.

Finally, from a mechatronic point of view, the two kinematic chains can be described as two independent blocks able to cooperate perfectly via the electronic architecture and thus the software described above.

The system provides for the presence, on the active kinematic chain, of a mechanical engagement element 6, capable of disengaging the relevant branch, in this case delegating the operation of the entire prosthesis to the passive part, in particular the damper assembly 4. The articular actuator assembly 5 is therefore provided with a removable mechanical engagement element 6 such that the actuator assembly 5 is switchable from a coupled condition to a decoupled condition. In the coupled condition, the actuator assembly 5 rotatably actuates the articular portion 3, i.e. the distal portion 2 with respect to the proximal portion 1. In the decoupled condition the distal portion 2 is coupled only to the damper assembly 4 for a predetermined angle of rotation.

The rationale for the presence of this mechanical engagement 6 lies in the fact that it is necessary to make possible a decoupling between the two chains, as they are both responsible for the functioning of the prosthesis, but at different operational stages. Thus, any fixed coupling between the two chains would lead to their being antagonistic, also adding operational problems that would be difficult to manage except with advanced control techniques.

The entire system is designed to guarantee a certain percentage of active support to the patient during the activities that require it (getting up, stairs, climbs). Other activities, such as natural walking, require only the hydraulic part, i.e. the damper assembly 4 comprising the valves 41 and the micromotors 410 that actuate them, to simulate satisfactorily the behaviour of a normally able-bodied person.

The active part consists of a frameless electric motor 50 with a diameter of 50 mm and a width of 16 mm, connected to a strain wave reduction gearbox 51 by means of a shaft 53, preferably made of aluminium and supported by ball bearings.

In the exemplary embodiment illustrated in the Figures, the motor 50 is integral with the proximal portion 1 and rotatably drives the distal portion 2. However, it is possible to reverse this configuration and make the motor integral to the distal portion 2 so as to rotate the proximal portion 1.

Strain wave reduction gearboxes are reduction gearboxes configured to collect the output motion by exploiting the deformability of a cylindrical element or elastic wheel 510, typically called flexspline, which meshes within an outer case provided with an inner-toothed crown 511. The elastic wheel 510 has several teeth fewer than the inner-toothed crown 511 and a smaller diameter than the inner-toothed crown 511. The meshing between the elastic wheel 510 and the inner-toothed crown 511 is ensured by a typically elliptical cam 512, inserted inside the elastic wheel 510 and capable of deforming the latter, so that the toothing of the now deformed elastic wheel 510 engages with the circular crown 511 with internal toothing. A ball bearing is interposed between cam and elastic wheel a to enhance movement and reduce friction. The rotating cam 512 performs the function of a carrier assembly and the elastic wheel 510 and inner-toothed crown 511 engage internally in two opposite zones. The elastic wheel 510 therefore ovalizes cyclically, engaging on the inner-toothed crown 511 and rotating in the opposite direction and at a much reduced angular speed with respect to the cam 512. The elastic wheel 510 is cup-shaped, with the same axis as the cam 512 connected to the input shaft 53, which is also the same axis 30 of the entire reduction gearbox 51 and the entire articular portion 3, so as to transmit the rotary motion output.

Although it is possible to use different types of reduction gearboxes, the strain wave reduction gearbox 51 is very advantageous as it allows the mechanical engagement element 6 of the kinematic chain to be created.

In this case, instead of being directly connected to the frame, i.e. to the distal portion part 2 connected to the joint 3, the elastic wheel 510 of the reduction gearbox is mounted onto it by means of a further bearing 513 and has two prism shaped outlets for the engagement adapted to cooperate with a suitably shaped distal portion part 2. In particular, the engagement element 6 comprises an actuating part fixed to the output of the reduction gearbox assembly and an actuated part integral with the distal portion 2, the actuating part and the actuated part being respectively provided with abutment and reciprocal fitting surfaces arranged on radial planes with respect to the axis of rotation 30.

The abutment surfaces are respectively provided on protrusions of the actuating part 60, or prism outlets, and on protrusions of the actuated part 61.

To cushion the impact due to the engagement contact of the abutment surfaces, it is possible to use interposed elements capable of absorbing energy, for example in polyurethane material. It is possible to provide for the use of these interposed elements, or of the same outputs of the reduction gearbox 51, as elements with high elasticity, characterized and known in the art, capable of giving information on the torque applied by the actuator assembly 5, which information is used by the control unit 9 in the control of the prosthesis.

The output of the reduction gearbox assembly 51, in particular the bottom wall of the cup-shaped elastic wheel 510, constitutes the said actuating part and is provided with the two said protrusions 60 protracting in the direction of the actuated part. The actuated part is integral to the distal portion 2 and is provided with two circular sector slots 62 in which the protrusions of the actuating part 60 are inserted. The slots 62 are separated from each other by an abutment element that constitutes two protrusions of the actuated part 61. The actuated part can consist only of the slots 62 in the frame, that is, the part of the distal portion 2 connected to the joint 3, or it can be a separate part, provided with the slots 62, and fixed integrally to the frame.

Both the protrusions of the actuating part 60 and the protrusions of the actuated part 61 are therefore symmetrical with respect to the axis of rotation 30. The protrusions of each part have abutment surfaces angularly spaced 180° apart.

The protrusions of the actuating part 60 and the protrusions of the actuated part 61 have angular extensions such that they can be angularly spaced from each other and constitute the decoupled condition or in contact with each other and constitute the coupled condition.

The control unit 9 is configured to drive the motor 50 in such a way that the driving part is moved in real time to an angular position such as to set the coupled condition or the decoupled condition.

In the decoupled condition, the protrusions of the actuating part 60 are positioned angularly, spaced from the protrusions of the actuated part 61 so as to constitute an end stop for the extension of the distal portion 2 and allow free flexion of the distal portion 2 for a predetermined angular amplitude.

The further degree of rotational freedom provided by the additional bearing 513 therefore allows the prosthesis, integral to the frame, i.e. to the part of distal portion 2 connected to the joint, to carry out the physiological walking movements without a mechanical constraint with the prism outlets of the reduction gearbox 51. Slots 62 on the frame, at appropriate angular positions, make it possible in the decoupled condition to rotate the knee without binding it to the actuating kinematic chain, delegating operation to the damper assembly 4 alone.

This case occurs, for example, during natural walking phases as illustrated in FIGS. 8 and 9: in this type of activity, the distal portion 2 must be able to rotate around the axis 30 of the joint in order to perform stance and swing, i.e. the position of full extension and flexion with rear kicking. This movement has a total maximum range of about 70°. In this condition the internal parts of the joint delegated to the active phase, i.e. the actuator assembly 5 consisting of motor 50, shaft 53 and strain wave reduction gearbox 51, must remain disengaged, as they would oppose the movement of the distal portion 2 itself, adding friction and inertia.

FIGS. 8*a*, 8*b* and 8*c* illustrate the decoupled condition, used during natural walking, in which an extension swing movement is possible with the active part disengaged. The distal portion 2 is released from the extending actuator and moves due to the effect of gravity without the need for energy input by the prosthesis.

FIG. 8*a* shows the stance or swing start condition, in which the protrusions of the actuating part 60 are positioned to allow the protrusions of the actuated part 61 to rotate freely under flexion.

FIG. 8*b* shows the flexing movement of the swing, of approximately 70°, in which the protrusions of the actuating part 60 move away with a free rotation from the protrusions of the actuated part 61, i.e. constrained only to the damper assembly 4.

FIG. 8*c* shows the extension with a rotation in the opposite direction to that shown in FIG. 8*c*, again by about 70°. The protrusions of the actuating part 60 in this case act as an end stop to the extension by coming into contact with the protrusions of the actuated part 61.

FIG. 9 shows the behaviour in terms of power delivered and absorbed by the two kinematic chains during the user's natural walk. In this phase, the engagement element 6 sets the actuator assembly 5 in a decoupled condition. The motor 51 is then disengaged, while the damper assembly 4 absorbs energy.

In the coupled condition, illustrated in FIGS. 10*a*, 10*b* and 11, the protrusions of the actuating part 60 and the protrusions of the actuated part 61 are in abutment with each other so as to actuate the rotation of the distal portion 2 in extension, or by reaction the proximal portion 1, in order to perform, for example, for the patient to rise from a seated position or climb a stairs.

In this coupled condition the mechanical contact is desired (engagement), to have active extension by the reduction gear inside the joint.

By applying a rotation to the actuating part of the engagement element 6 it is possible to engage the protrusions of the actuating part 60, i.e. the two prism outlets, with the protrusions of the actuated part, i.e. with the frame by contacting the respective abutment surfaces, as shown in FIG. 10*a*.

From this moment on, it is possible to operate the prosthesis by activating the actuator assembly 5, as illustrated in FIG. 10*b*, for an active extension that can reach approximately 115°.

The action of actuator assembly 5 is preferably unidirectional, only in extension. Bidirectional movement is not required in this case, since the only active action required is the extension of the prosthesis. Flexion, on the other hand, does not need to be controlled by a reduction gear, as it is sufficient that it occurs as a result of the inertial forces applied by the patient, and that it is regulated via the damper assembly 4, which is bidirectionally bound to the prosthesis. To carry out free flexion, through the inertial forces applied by the patient, it is sufficient that the output of the reduction gearbox 51 is moved in advance in such a way as to distance the prism outlets 60 from the engagement position, in order not to oppose the inertial movement of the distal portion 2.

FIG. 11 illustrates the behaviour in terms of power delivered and absorbed by the two kinematic chains when the user rises from a seated position. In this phase, the mechanical engagement element 6 sets the actuator assembly 5 in the coupled condition and the motor 51 is engaged and delivers power by actuating the extension prosthesis.

It is possible to use an alternative configuration in which, instead of providing circular sector slots 62, the actuating part and the actuated part are substantially disc-shaped and placed parallel to each other and rotatable around the axis of rotation 30, each part having its own protrusions oriented towards the opposite part.

It is also possible to provide a single protrusion not symmetrical with respect to the rotation axis 30 in the actuating part or in the actuated part.

Furthermore, a coupled condition can be provided such as to allow an active actuation of the actuator assembly even during prosthesis flexion.

The prosthetic device disclosed makes it possible to obtain a high efficiency and low consumption operation of a significant versatility: the prosthesis can in fact operate both in passive mode only with the hydraulic unit, and in active mode with the hydraulic unit and reduction gearbox engaged. The modular architecture ensures that the prosthesis can work even without the physical presence of the reduction gearbox, and only with the hydraulic unit.

The device has reduced dimensions and weights compared to other active prostheses, in particular a shape that falls within the anthropometric dimensions.

The invention claimed is:

1. A prosthetic device, adapted to replace at least in part a limb of a user, comprising a proximal prosthetic portion adapted to be coupled to a limb segment of the user and a distal prosthetic portion, the proximal prosthetic portion and the distal prosthetic portion being inter-connected by means of a joint portion, said joint portion comprising an articular actuator assembly for rotatably actuating said distal portion with respect to said proximal portion around an axis of rotation, a damper assembly being provided connected to said articular portion and adapted to absorb energy when a torque is applied between said proximal portion and said distal portion, wherein the articular actuator assembly is provided with a removable mechanical engagement element such that the actuator assembly is switchable from a coupled condition in which it rotatably drives said distal portion with respect to said proximal portion to a decoupled condition in which said distal portion is coupled only to said damper assembly for a predetermined angle of rotation, wherein the articular actuator assembly comprises an electric motor and a reduction gearbox, which reduction gearbox is connected at an input with the motor and at an output with said engagement element, wherein said engagement element comprises an actuating part connected to the output of the reduction gearbox and an actuated part integral with the distal portion, the actuating part and the actuated part respectively provided with abutment and reciprocal fitting surfaces arranged on radial planes with respect to said rotation axis, and wherein the abutment surfaces are respectively provided on at least one protrusion of the actuating part and on at least one protrusion of the actuated part, said protrusions having angular extensions such that in said decoupled condition the protrusion of the actuating part is positioned angularly, spaced from the protrusion of the actuated part so as to constitute an end stop for the extension of the distal portion and allow free flexion of the distal portion for a predetermined angular amplitude, while in said coupled condition the protrusions respectively of the actuating part and the actuated part are in abutment with each other so as to actuate the relative rotation of the distal portion with respect to the proximal portion in extension.

2. The device according to claim 1, wherein one or more sensors and a control unit are provided, which control unit is connected with said sensors and is configured to set the actuator assembly in a coupled or a decoupled condition based on data received from the sensors.

3. The device according to claim 1, wherein the control unit is configured to drive the motor in such a way that the actuating part is moved in real-time in an angular position such as to set said coupled condition or said decoupled condition.

4. The device according to claim 3, wherein the control unit is configured to actuate the motor in such a way that when a patient is in a seated position the actuating part is in said decoupled condition in a "trailing" mode such that the actuating part is maintained in real-time at a constant angular distance from the actuated part, during the patient's rise from said seated position the actuating part is brought into contact with the actuated part to set said coupled condition and upon the patient reaching a standing position the actuating part is brought to an angular getaway distance from the actuated part such as not to hinder walking.

5. The device according to claim 1, wherein the at least one protrusion of the actuating part and the at least one protrusion of the actuated part each comprises protrusions symmetrical with respect to the axis of rotation, which said protrusions of each of the actuating part and the actuated part have at least two of said abutment surfaces angularly spaced 180° apart.

6. The device according to claim 5, wherein said reduction gearbox is a strain wave reduction gearbox.

7. The device according to claim 6, wherein the output of the reduction gearbox constitutes said actuating part and is provided with two of said protrusions protracting in the direction of the actuated part, the actuated part being integral with the distal portion and provided with two circular sector slots into which said two protrusions of the actuating part are inserted, said slots being separated from each other by an abutment element constituting two of said protrusions of the actuated part.

8. The device according to claim 1, wherein the damper assembly comprises a hydraulic cylinder provided with one or more valves actuated by said control unit.

* * * * *